US008636837B2

(12) United States Patent  
Nonnenmacher (10) Patent No.: US 8,636,837 B2  
(45) Date of Patent: Jan. 28, 2014

(54) SOLIDS SEPARATOR

(71) Applicant: Duerr Dental AG, Bietigheim-Bissingen (DE)

(72) Inventor: Eberhardt Nonnenmacher, Ingersheim (DE)

(73) Assignee: Duerr Dental AG (DE)

( * ) Notice: Subject to any disclaimer, the term of this patent is extended or adjusted under 35 U.S.C. 154(b) by 0 days.

(21) Appl. No.: 13/735,161

(22) Filed: Jan. 7, 2013

(65) Prior Publication Data

US 2013/0118356 A1     May 16, 2013

Related U.S. Application Data

(63) Continuation of application No. PCT/EP2011/003433, filed on Jul. 9, 2011.

(30) Foreign Application Priority Data

Jul. 29, 2010 (DE) .................... 20 2010 010 802 U (51) Int. Cl.  
    *B01D 19/00*     (2006.01)

(52) U.S. Cl.  
    USPC ................... 96/165; 96/212; 96/167; 96/168; 95/259

(58) Field of Classification Search  
    USPC ........... 96/212, 165, 167, 168, 209, 210, 211; 95/259  
    See application file for complete search history.

(56) References Cited

U.S. PATENT DOCUMENTS

| | | | | |
|---|---|---|---|---|
| 3,359,708 | A | * | 12/1967 | Barber ........................... 96/167 |
| 4,919,826 | A | * | 4/1990 | Alzner ........................... 210/788 |
| 5,018,971 | A | | 5/1991 | Trawoger et al. |
| 2006/0065594 | A1 | | 3/2006 | Armstrong et al. |
| 2008/0099390 | A1 | | 5/2008 | Plath |

FOREIGN PATENT DOCUMENTS

| | | |
|---|---|---|
| DE | 35 42 160 A1 | 6/1987 |
| EP | 0 400 431 A2 | 12/1990 |
| WO | 95/12365 A1 | 5/1995 |
| WO | WO 0130707 A1 * | 5/2001 |

* cited by examiner

*Primary Examiner* — Duane Smith  
*Assistant Examiner* — Douglas Theisen  
(74) *Attorney, Agent, or Firm* — Factor Intellectual Property Law Group, Ltd.

(57) ABSTRACT

A sedimentation separator for separating solid fractions from a mixture consisting of air, liquid and solids fractions comprises a sedimenting vessel to which an air-separating unit is connected upstream. In an intermediate vessel arranged between the air-separating unit and sedimenting vessel there is arranged a float which closes off an air duct when the level of sediment in the sedimenting vessel has reached a predetermined height. Liquid purified by sedimentation is suctioned off from the upper end of the sedimenting vessel by means of a jet pump.

21 Claims, 5 Drawing Sheets

SOLIDS SEPARATOR

CROSS-REFERENCE TO RELATED APPLICATIONS

The present application is a continuation of International Patent Application No. PCT/EP2011/003433 filed on Jul. 9, 2011 which claims priority to German utility patent no. 20 2010 010 802.0 filed Jul. 29, 2010. The full disclosure of both applications are incorporated herein by reference in their entirety.

BACKGROUND OF THE INVENTION

1. Field of the Invention

The invention relates to a separator for removing solid fractions from a mixture of air, liquid and solids.

2. Description of Related Art

Three-phase mixtures of air, liquid and solids are produced during machining of objects. These mixtures cannot be disposed of directly in the public drainage system for environmental reasons. An example of such mixtures is a mixture of air, body fluids and amalgam particles which accumulates when drilling out amalgam fillings at a dental workplace. The amalgam must not be disposed of in the public wastewater system, but must instead be collected separately and supplied for correct disposal.

Various processes are used to separate the solid particles. Centrifugation of the solids has proven particularly effective for separating small particles. However, the corresponding centrifuges are expensive and, in the case of waste waters which contain amalgam particles, the legislative bodies of some countries only regard it as sufficient when these particles are separated from the liquid by sedimentation.

Accordingly, these use amalgam separators which operate according to the sedimentation principle.

These known sedimentation tanks generally have an outlet which is in communication with the actual sedimentation chamber by way of an overflow.

The sedimentation units generally comprise a collection tank which contains the sedimented amalgam, and this collection tank has to be exchanged at intervals for an empty tank.

The effectiveness of the sedimentation for an air-containing mixture is impaired by bubbles and/or foam, particularly when the liquid contains foam-forming substances such as protein or saponines or cleaning agents.

SUMMARY OF THE INVENTION

An object of the present invention, therefore, is to provide a solids separator which operates according to the sedimentation principle and which also separates solids effectively in mixtures containing air or another gas.

This object may be achieved by a separator for removing solid particles from a mixture of air, liquid and solid particles, comprising
 a sedimentation unit which has a mixture inlet and a liquid outlet and a collection tank for retained solid fractions, and
 an air-separating unit having an air outlet and a mixture outlet, wherein the mixture outlet is connected to the mixture inlet of the sedimentation unit.

In the separator according to the invention, air fractions of the mixture do not reach the sedimentation chamber. Therefore the merely two-phase mixture of liquid and solid fractions in the sedimentation chamber can separate effectively under gravity.

Also, the sedimentation process is not adversely affected by an air flow passing through the sedimentation chamber.

Advantageous further developments of the invention are described in further embodiments.

In a sedimentation unit in which the liquid with a reduced solid content is discharged by way of an overflow, there is a risk of liquid being spilled when the collection tank is removed. Since, in the case of a mixture collected at a dental workplace, this liquid also contains germs and possibly viruses, it is desirable to prevent liquid from being spilled when servicing or exchanging a collection tank of the sedimentation unit.

This object may be achieved if the liquid outlet of the sedimentation unit is connected to a liquid pump.

In the separator according to the invention, an overflow is not provided and the level of the liquid located in the sedimentation unit is always below the liquid outlet of the separator since the liquid pump provided according to the invention draws off liquid from such a point. The sedimentation unit or a collection tank forming part thereof can therefore be moved by hand and tilted or exposed to accelerations without liquid escaping into the environment.

There is no need to provide a complex mechanical pump if the liquid pump is a jet pump. To withdraw cleaned liquid, a jet pump is used whereof the motive fluid is the delivered air. A jet pump of this type is mechanically simple in terms of its construction and also functions in trouble-free manner over a long operating period.

In the case of suction machines which are used at dental workplaces, it is possible to distinguish between wet suction machines and dry suction machines. The term wet suction machine here refers to a suction machine which also functions reliably over a long operating period in the presence of liquid. An example of a wet suction machine of this type is a water ring pump in which a circulating water ring is part of the delivery device. In any event, pumps of this type have to be designed to withstand a liquid and/or steamy environment over a long period. A dry suction machine refers to the type usually used for delivering dry gases. Typical examples of such dry suction machines used in dentistry are piston machines and side channel machines as well as rotor machines with an axially acting rotor or radially acting rotor.

It is proposed that a wet suction machine, in particular a water ring pump, be used at the mixture outlet of the liquid pump for the purpose of generating the negative pressure required at the dental workplace.

Alternatively, it is proposed that the mixture of air and liquid obtained at the outlet of the liquid pump be supplied to a second air separating unit whereof the air outlet is then connected to the inlet of a suction fan, which can then be a dry suction machine.

With a separator, wherein the air-separating unit has a chamber which is in communication with the sedimentation unit and in which a level sensor is arranged, this level sensor being used to control a position of a control body with respect to a valve seat of an air channel or a mixture channel in order to throttle or block the air channel or the mixture channel, the user of a suction unit comprising such a separator is made expressly aware that the capacity of the sedimentation unit has been reached or exceeded by a decrease in, or failure of, the suction power.

The compulsory throttling or blocking of the suction air flow is achieved in mechanically simple manner if the level sensor comprises a float and the float is mechanically connected to the control body.

If the control body is pre-tensioned in a closed position by a spring and can be locked in an open position by a releasable locking mechanism and in that the locking mechanism can be disengaged by the level sensor, it is ensured that the separator operates with a constant air throughput when the maximum fill level of the solid sediment is not yet reached and promptly reduces or completely stops the air throughput when the maximum permissible fill quantity is reached or exceeded.

A level sensor comprising a sensor plate which is supported on the base of the collection tank by way of a spring can be assembled here very simply and reliably from a small number of parts.

An elastomer block spring as a spring is loaded according to the weight of the sediment bed and can be constructed simply and in a manner which is suitable for contaminating environmental conditions.

An elastomer block spring having a liquid-tight surface skin is advantageous here in terms of a fluidic sealing of the interior of the block spring with respect to the interior of the sedimentation chamber.

If the sensor plate is pivotally supported by the collection tank, it is readily possible to derive a useful movement with a transverse component with respect to the device axis from the weight-related positional change of the sensor plate. A movement of this type is suitable for releasing a locking mechanism with which the control body is held in an open position.

A separator, wherein the control body supports a rod which is guided into an interior of the collection tank and supports a locking head at its free end, gives a solution for simple locking of the control body controlling the air throughput through the separator in an open position, which is maintained until the maximum fill level in the sedimentation unit is reached.

A locking mechanism comprising a counter-locking device which cooperates with the locking head of the rod for the control body is notable here for a particularly simple mechanical construction.

The counter-locking device may be constructed as a wire which can be moved by a cam body supported by the sensor plate with a transverse movement component with respect to the rod axis or which can be cut by a blade moved along with the sensor plate. This is one alternative for a releasable locking mechanism for the control body.

Another alternative is a counter-locking arm which is supported by the pivotally mounted sensor plate.

A rod supporting the control body, wherein the rod is supported by two parallel-spaced membranes, enables the control body to be axially displaceably mounted with a low degree of friction using mechanically simple means.

It is to be understood that the aspects and objects of the present invention described above may be combinable and that other advantages and aspects of the present invention will become apparent upon reading the following description of the drawing and detailed description of the invention.

BRIEF DESCRIPTION OF THE DRAWINGS

The invention is explained in more detail below with reference to exemplary embodiments with the aid of the drawings, which show.

DETAILED DESCRIPTION OF PREFERRED EMBODIMENTS

While this invention is susceptible of embodiment in many different forms, there is shown in the drawing and will herein be described in detail one or more embodiments with the understanding that the present disclosure is to be considered as an exemplification of the principles of the invention and is not intended to limit the invention to the embodiments illustrated.

Reference throughout this description to features, advantages, objects or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, any discussion of the features and advantages, and similar language, throughout this specification may, but does not necessarily, refer to the same embodiment.

Figure 1:
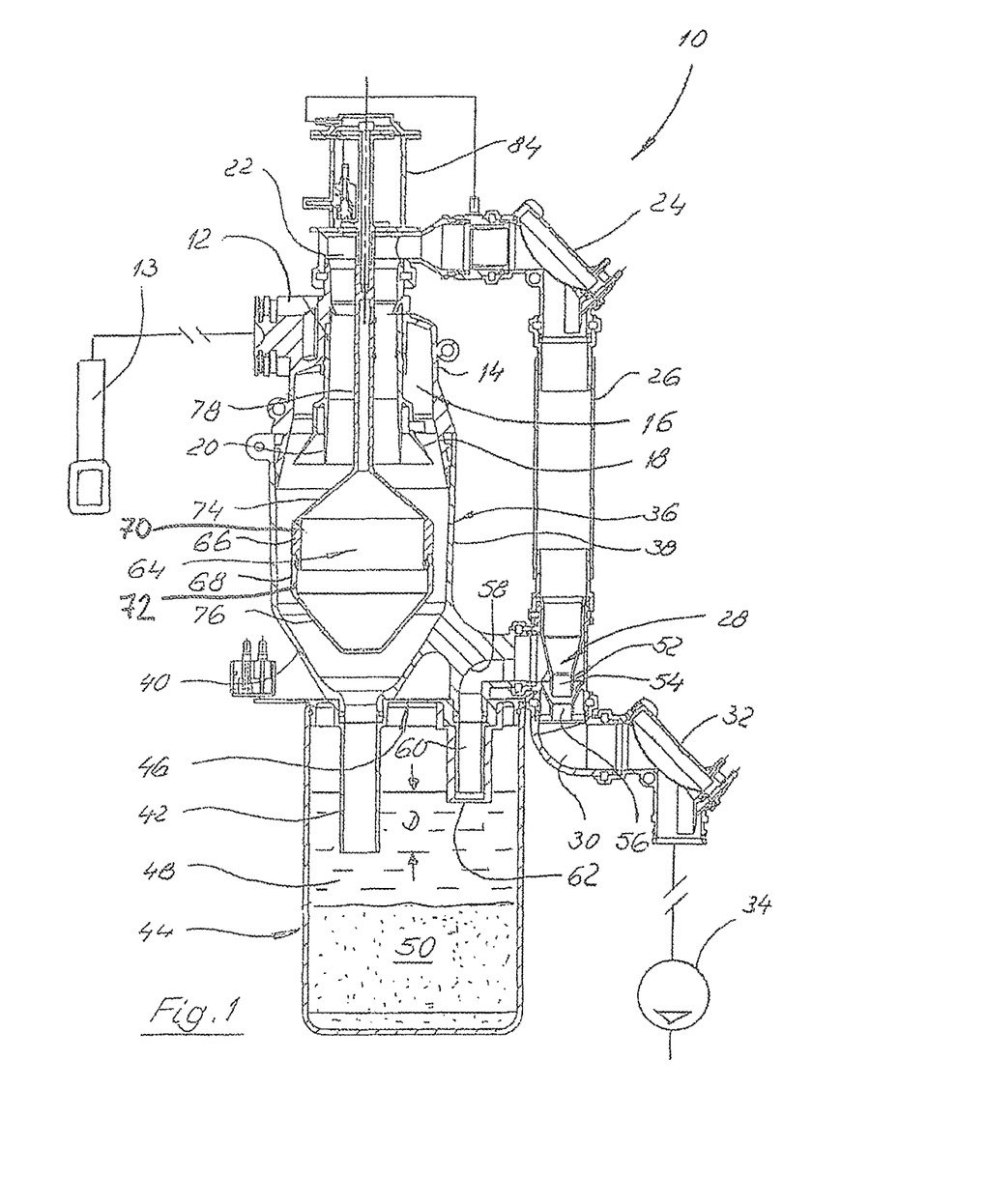
FIG. 1 which is an axial section through a sedimentation amalgam separator with a removable collection tank and liquid extraction pump.

In FIG. 1, an amalgam separator which operates according to the sedimentation principle is denoted as a whole by 10.

This separator comprises an inlet connection piece 12, which is acted upon from a dental workplace with a mixture of air, body fluids and solid particles (bone fragments, amalgam particles etc.). A suction cannula 13, which is used to extract rinsing water, saliva, blood and drilling debris from the mouth of a patient, is shown schematically as a source for this mixture.

The inlet connection piece 12 is aligned horizontally and leads tangentially into a circumferential wall 14 of a cyclone 16 with a vertical axis.

Provided concentrically to the circumferential wall 14, with a radial spacing to the inside, there is a conducting cavity 18 which widens conically downwards and is positioned on a cylindrical air outlet channel 20 such that the lower edges of the outlet channel 20 and conducting cavity 18 are located in a transverse plane.

In the annular space formed between the conducting cavity 18 and the outer surface of the outlet channel 20 on the one hand and the inner surface of the circumferential wall 14 on the other, the mixture supplied through the inlet connection piece 12 spirals slowly downwards, whereby the liquid and solid constituents of the mixture are pressed against the inner surface of the circumferential wall 14 by centrifugal force. The lighter air fractions then move inwards and arrive in the cylindrical outlet channel 20.

By way of the outlet channel 20 and an attached angular piece 22, a pilot angle valve 24, a vertical connecting line 26, a jet pump 28, a deflection angle 30 and a further pilot angle valve 32, the air flow is extracted by a suction machine 34 illustrated merely schematically in the drawing, from where the air is then delivered to the environmental atmosphere.

In the exemplary embodiment considered here, the suction machine 34 is a wet suction machine in the form of a water ring pump.

The liquid and solid fractions of the supplied mixture which are separated in the cyclone 16 arrive from the cyclone 16 in an intermediate chamber 36 with a cylindrical circumferential wall 38 and a conical base wall 40.

The lower end of the conical funnel-shaped base wall 40 is provided with a discharge connection piece 42 which leads into the interior of a cup-shaped collection tank 44 which is open at the top. This is held by a cover plate 46 which is connected to the intermediate tank 36.

The mixture of liquid and solid fractions which is discharged from the end of the discharge connection piece 42 arrives inside the collection tank 44 and there forms a liquid volume 48 and a sediment volume 50 located beneath it.

The mixture of liquid and solid fractions which is supplied from the intermediate tank 36 is separated by gravity inside the collection tank 44, so that the top liquid layer in the collection tank 44 has an effectively reduced solid content.

The jet pump 28 draws from this top liquid layer.

The jet pump 28 has an injector 52 (located at the top in the drawing) which is acted upon by the suction air and tapers downwards. The end of the injector 52 projects with an annular gap 54 into a collector 56 which tapers conically downwards.

By way of an angled channel 58, the annular gap 54 communicates with a suction pipe 60 which hangs down from the cover plate 46.

A slim, cup-shaped filter body 62, which can consist of a sintered filter material, for example, is pushed over the suction pipe 60. The filter body 62 only needs to have filter properties in the portion located below the end of the suction pipe 60.

As shown in the drawing, the lower end of the suction pipe 60 is located a distance D above the lower end of the discharge connection piece 42. This prevents the mixture of liquid and solid fractions which is discharged from the discharge connection piece 42 from arriving directly at the suction connection piece 60. Instead, this mixture has to remain a certain length of time inside the collection tank 44 so that there is sufficient time for the sedimentation of the solid fractions.

The amalgam separator described above operates as follows:

The mixture of air, liquid and solid particles enters the cyclone 16 by way of the inlet connection piece 12. The air fractions are separated there and extracted by way of the outlet channel 20.

The liquid and solid fractions of the mixture arrive in the collection tank 44 by way of the intermediate tank 36. The majority of the solid fractions deposit there, thereby increasing the sediment volume 50. Clarified liquid in the top layer of the liquid volume 48 is extracted therefrom by the jet pump 28 which uses the air extracted by the suction machine 34 as a motive fluid.

If the collection tank 44 needs exchanging due to the sediment volume 50 reaching a maximum permissible level, the collection tank 44 is removed from the cover plate 46. If the tank is shaken or tilted as it is removed, this does not cause any spillage of the liquid still inside the collection tank 44 since the liquid level is at the lower end of the suction pipe 60 and this is clearly below the upper edge of the collection tank 44.

The removed collection tank 44 can then be closed by a suitable cover and sent to a waste management company. An empty collection tank is then fitted.

It can be seen that the amalgam separator can therefore be reliably handled without a risk of the environment being contaminated by germ-containing liquid.

To indicate clearly to the user of a suction system containing the separator that the collection tank 44 needs exchanging, a mechanism is integrated in the separator, which throttles the suction air flow, or interrupts it completely, when the maximum permissible level of the sediment volume 50 is reached.

This mechanism comprises a control body 64 which comprises two tightly connected shell parts 66, 68. These each have a cylindrical wall 70 and 72 located in the central plane and an end wall 74 and 76 tapering conically to the upper and lower end of the control body 64 respectively.

Figure 2:
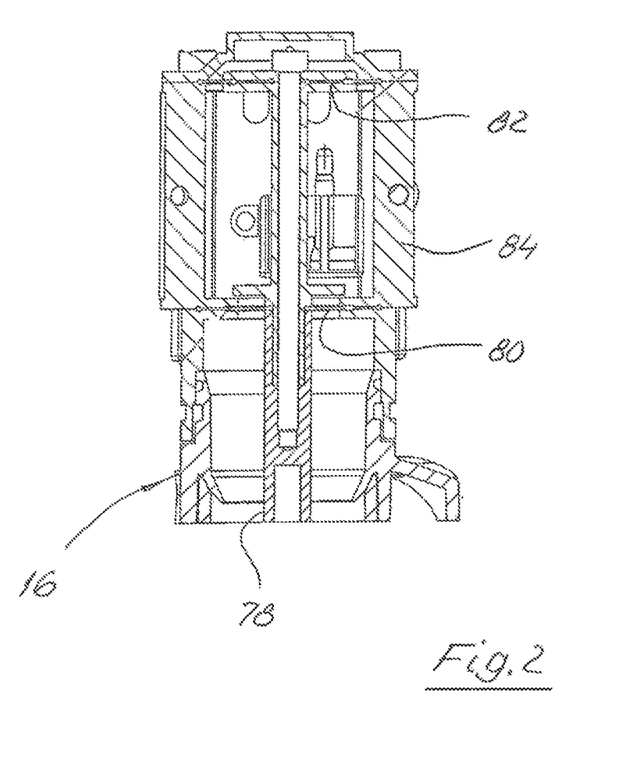
FIG. 2 which is an enlarged axial section through an axial guide for a throughput control body of the amalgam separator according to FIG. 1; which axial guide is provided at the upper end of the amalgam separator.

The control body 64 is supported by a hollow rod 78 which is arranged with a large radial play in the interior of the outlet channel 20 and is mounted by way of two spaced membranes 80, 82 (see FIG. 2) on a cylindrical attachment 84 of the cyclone 16.

The upper conical end wall 74 of the control body 64 constitutes a control surface which cooperates with the lower end of the cylindrical outlet channel 20.

At the same time, the control body 64 forms a float which is raised when liquid rises back into the interior of the intermediate tank 36. The liquid rises back in this way when the upper delimiting surface of the sediment volume 50 reaches the lower end of the filter body 62. This then blinds and the jet pump 28 is only able to extract liquid from the collection tank 44 in reduced measure or no longer at all.

Liquid which is separated in the cyclone 16 therefore remains together with the contained solid fractions inside the collection tank 44 and rises inside the intermediate tank 36. This causes the control body, which at the same time acts as a float, to be displaced axially upwards, which results in the passage between the lower end of the outlet channel 20 and the upper side of the end wall 74 being reduced and finally closed completely.

The dentist operating at the workplace equipped with the amalgam separator is thus made aware of the fact that the collection tank 44 is full and needs exchanging as a result of the reduction in the suction power or complete loss of suction power.

Figure 3:
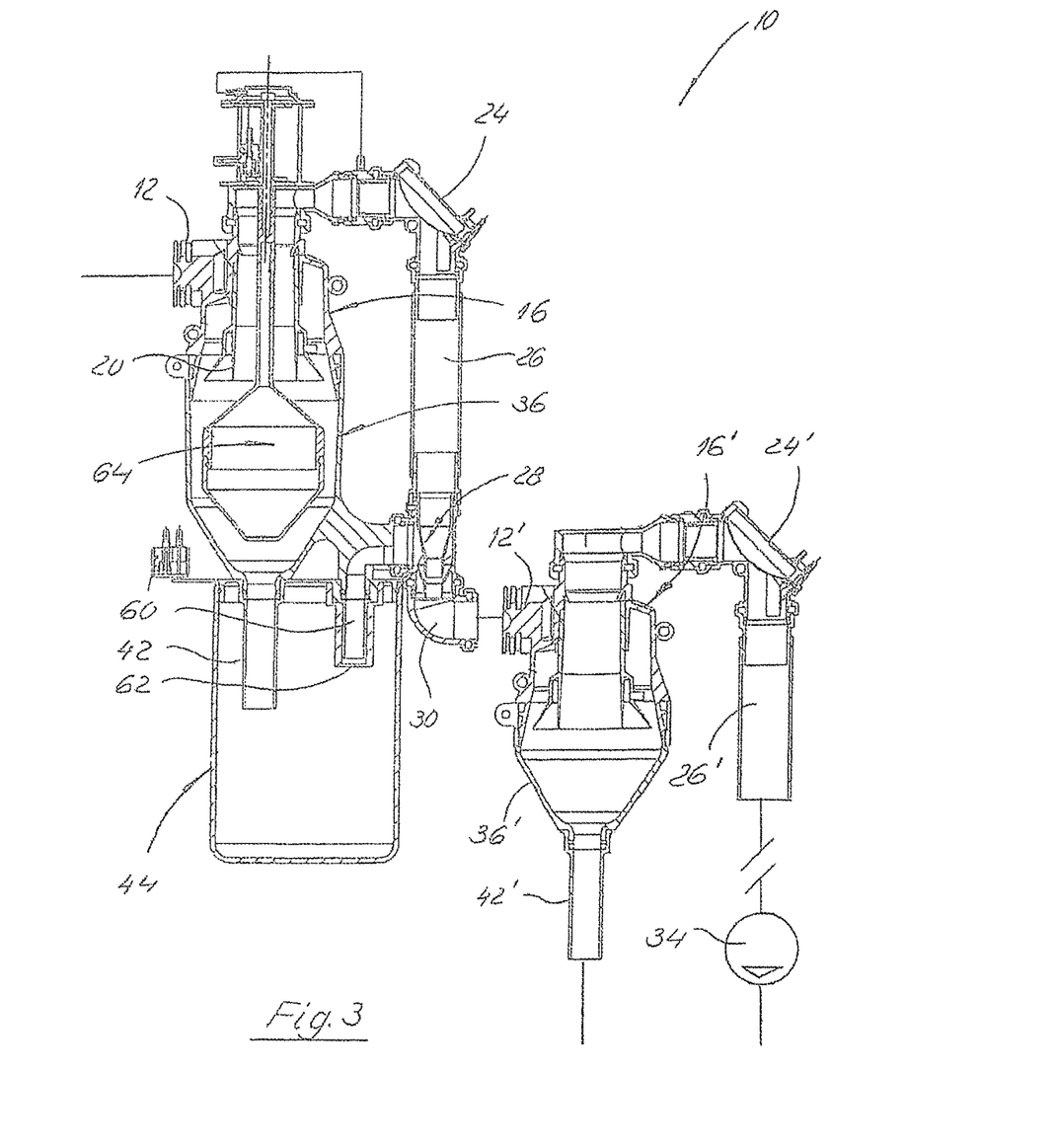
FIG. 3 which is an amalgam separator according to FIG. 1 with a series-connected further air separator for use in a dental workplace, for which a dry suction machine is provided.

If the amalgam separator shown in FIG. 1 is used in conjunction with a dry suction machine, then a further cyclone 16' is connected downstream thereof according to FIG. 3, which cyclone 16' is of a similar construction to the cyclone 16 and therefore does not need describing in detail. However, the cyclone 16' does not include those components which serve to indicate the fill level of the collection tank 44 and the compulsory reduction or compulsory switching-off of the suction power.

It is clear that this second cyclone 16' can be realised using substantially the same parts as the cyclone 16.

Figure 4:
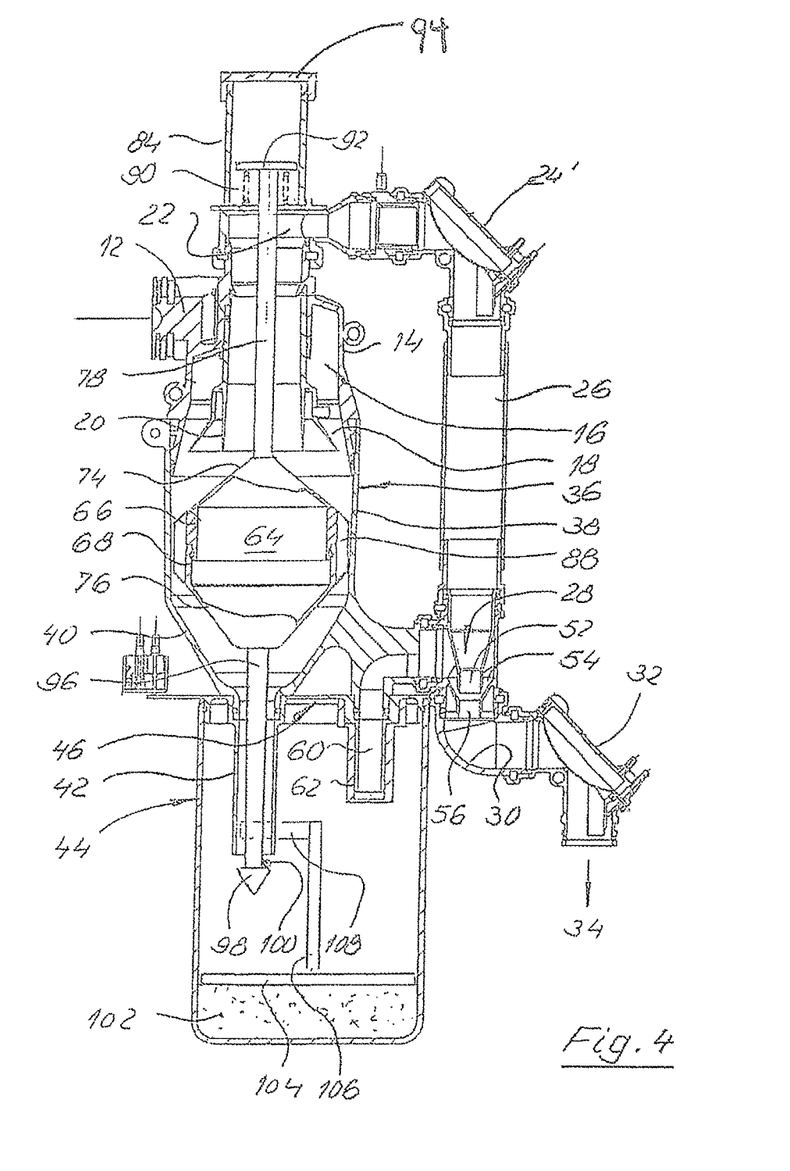
FIG. 4 which is a similar view to FIG. 1, in which a locking device for an air-throughput control body is provided.

FIG. 4 shows a further modified amalgam separator in which the control body 64 is held in a fully open position until the maximum permissible sediment level in the collection tank 44 is reached.

The control body 64 is now additionally equipped on its outer surface with guide wings 88 which are distributed in a star shape in the circumferential direction and by way of which it moves over the inner surface of the intermediate tank 36 with little friction.

The rod 78 is pre-tensioned in the closed position by a spring 90 in the attachment 84, which acts on it by way of a spring seat 92. The spring seat 92 is accessible from the outside by way of a removable cap 94 in order to press it downwards in opposition to the force of the spring 90.

Securely attached to the lower end of the control body 64, there is a further rod 96, which is provided with a radially projecting conical head 98. In an operating position, this projects beyond the lower end of the discharge connection piece 42 and, when the spring seat 92 is pressed downwards as described above, the conical ramp face of the head 98 moves over a locking wire 100 which is tensioned transversely through the interior of the collecting tank 44. This can be a plastic wire, the ends of which are securely welded to the circumferential wall of the collection tank 44.

Inserted in the bottom portion of the collection tank 44, there is an elastomer block spring 102 which is made from an elastomeric porous material with a fluid-tight outer skin A sensor plate 104, which is guided up to the circumferential wall of the collection tank 44 with a relatively large sliding play, rests on the block spring 102. The sensor plate 104 can be made for example from a low-friction plastic material such as PE or PA.

The upper side of the sensor plate 104 supports a holding plate 106. For clearer illustration, this is shown located on the axis of the collection tank 44. In practice, it is arranged adjacent to the end of the discharge connection piece.

The upper end of the holding plate 106 supports a horizontal blade 108 which extends away from it to the left in the drawing and can be formed by a ground metal plate, similar to a razor blade.

When the tank is empty, the lower edge of the blade 108 projects a predetermined distance beyond the locking wire 100.

If, during operation of the amalgam separator 10, a sediment volume 50 forms over the sensor plate 104, the block spring 102 is compressed increasingly by the weight of the sediment volume. The rigidity of the block spring 102 is selected so that the blade 108 arrives at the locking wire 100 precisely upon reaching the maximum permissible sediment volume 50 up to a predetermined tolerance amount, which can be for example approximately 10-15%.

Upon further separation of amalgam and other solids, the blade 108 then comes into engagement with the plastic locking wire 100 and then cuts through this. The head 98 of the rod 96 is then released and, under the pre-tension of the spring 90, the control body 64 is then moved upwards so that its end wall 74 closes the lower end of the outlet channel 20. There is now no longer any suction power at a suction cannula 13 connected to the inlet of the amalgam separator 10, which alerts the user to the fact that the collection tank 44 has to be exchanged for an empty one.

In a modification, the blade 108 can also be mounted at the upper end of the holding plate 106 in such a way that the blade 108 drops outwards and downwards so that, when the sensor plate 104 is lowered, a relative movement takes place simultaneously between the blade 108 and the locking wire 100. This improves the cutting action.

As another alternative, it is also possible to mount a cam face at the end of the holding plate 106, for example in the form of an outwardly and downwardly angled rod, instead of the blade 108, so that, when the sensor plate 104 moves downwards, the locking wire 100 is then pressed to the right in FIG. 4 without interference, causing the head 98 to likewise be released and the control body 64 to then be moved into the closed position under the pre-tension of the spring 90.

Figure 5:
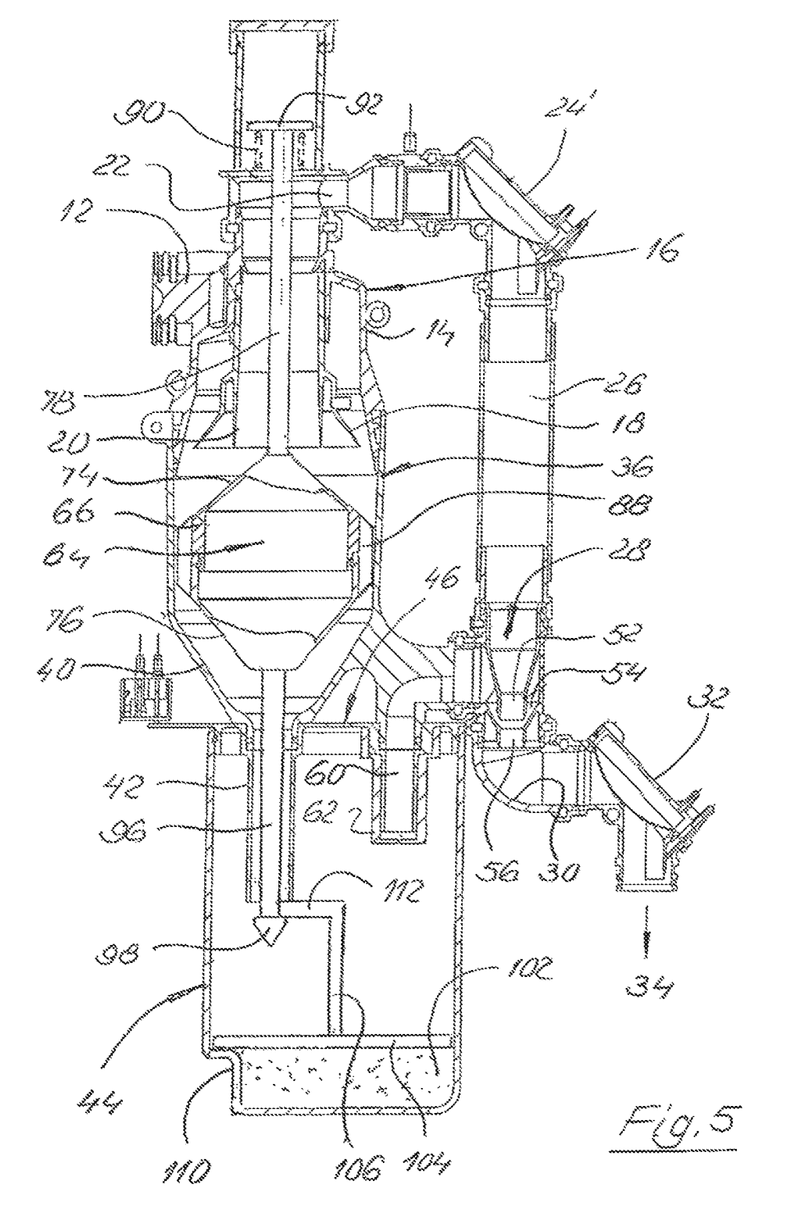
FIG. 5 which is a similar view to FIG. 4, but showing a modified locking device for the air-throughput control body.

The exemplary embodiment according to FIG. 5 corresponds substantially to that of FIG. 4 and therefore, in this regard, does not need to be explained again in detail.

However, the sensor plate 104 is now tiltably mounted at its one end (positioned on the left in the drawing) on a step 110, which is incorporated in the circumferential region (positioned on the left in FIG. 5) between the base and circumferential wall of the collection tank 44. The end of the holding plate 106 rigidly supports a locking arm 112 which cooperates with the head 98.

If a sediment volume of sufficient mass builds up over the sensor plate 104, the sensor plate 104 is pivoted about the edge of the step 110 in opposition to the force of the block spring 102. If the sensor plate 104 pivots far enough, the locking arm 112 is then released from the head 98 of the rod 96, causing the control body 64 to be moved back into the closed position under the force of the spring 90.

Large numbers of the amalgam separator described above and shown in the drawing can be realised economically from plastic injection-moulded parts. It has good operational reliability since it is not possible to continue working when a predetermined maximum permissible final sediment volume is reached in the collection tank.

With this, it is also ensured that, when the collection tank is removed, no liquid spills from the tank if this is tilted, for example, or removed in jolting manner.

The amalgam separator can be used directly on wet suction machines and can also be used on dry suction machines when a further air separator, which can be composed of substantially the same components as those of the amalgam separator, is connected to it in series.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A separator for removing solid particles from a mixture of air, liquid and solid particles, comprising;
   a solid-separating unit configured to separate solid particles from a two-phase mixture of liquid and solid particles and to retain the separated solid particles in a collection tank, wherein the solid-separating unit has a mixture inlet and a liquid outlet,
   an air-separating unit having an air outlet and a mixture outlet, wherein the mixture outlet is connected to the mixture inlet of the solid-separating unit and,
   a jet pump having a motive fluid inlet, a suction inlet and a mixture outlet, the motive fluid inlet being connected to the air outlet of the air-separating unit and the suction inlet being connected to the liquid outlet of the solid-separating unit, wherein the mixture outlet of the jet pump is configured to be connected with a suction machine, and,
   wherein the jet pump comprises a vertically oriented injector which tapers, downwards and projects with an annular gap into a collector which tapers downwards, and wherein the injector is connected to the motive fluid inlet, the annular gap is connected to the suction inlet and the collector is connected to the mixture outlet of the jet pump.

2. The separator according to claim 1, wherein the liquid outlet of the solid-separating unit is connected to a liquid pump.

3. The separator according to claim 2, wherein the liquid pump is a jet pump having a motive fluid inlet, a suction inlet, the motive fluid inlet being connected to the air outlet of the air-separating unit and the suction inlet being connected to the liquid outlet of the solid-separating unit, wherein the jet pump comprises a mixture outlet which is configured to be connected to a suction machine.

4. The separator according to claim 3, wherein a wet suction machine is connected to the mixture outlet of the jet pump.

5. The separator according to claim 3, wherein the mixture outlet of the jet pump is connected via a second air-separating unit to an inlet of a dry suction machine.

6. The separator according to claim 1, wherein the air-separating unit has a chamber which is in communication with the solid-separating unit and in which a level sensor is arranged, this level sensor being configured to control a position of a control body with respect to a valve seat of an air channel or a mixture channel in order to throttle or block the air channel or the mixture channel, respectively.

7. The separator according to claim 6, wherein the level sensor comprises a float that is mechanically connected to the control body.

8. The separator according to claim 6, wherein the control body is pre-tensioned in a closed position by a spring and is capable of being locked in an open position by a releasable locking mechanism, and wherein the locking mechanism is capable of being disengaged by the level sensor.

9. The separator according to claim 8, wherein the collection tank comprises a base and the level sensor comprises a sensor plate which is supported on the base of the collection tank by a spring.

10. The separator according to claim 9, wherein the spring is an elastomer block spring.

11. The separator according to claim 10, wherein the elastomer block spring has a liquid-tight surface skin.

12. The separator according to claim 9, wherein the sensor plate is pivotally supported by the collection tank.

13. The separator according claim 9, wherein the control body supports a rod which is guided into an interior of the collection tank and supports a locking head at its free end.

14. The separator according to claim 13, further comprising a counter-locking device which cooperates with the locking head of the rod.

15. The separator according to claim 14, wherein the counter-locking device is constructed as a wire which is configured to be moved by a cam body supported by the sensor plate with a transverse movement component with respect to the rod axis.

16. The separator according to claim 14, wherein the counter-locking device is constructed as a wire which is configured to be cut by a blade moved along with the sensor plate.

17. The separator according to claim 14, wherein the sensor plate supports a counter-locking arm.

18. The separator according to claim 6, wherein the control body is supported by a rod, said rod being supported and axially displaceable by two parallel-spaced membranes.

19. The separator according to claim 1, wherein the solid-separating unit is a sedimentation unit.

20. A separator for removing solid particles from a mixture of air, liquid and solid particles, comprising:
a solid-separating unit configured to separate solid particles from a two-phase mixture of liquid and solid particles and to retain the separated solid particles in a collection tank, wherein the solid-separating unit has a mixture inlet and a liquid outlet;
an air-separating unit having an air outlet and a mixture outlet, wherein the mixture outlet is connected to the mixture inlet of the solid-separating unit; and,
a jet pump having a motive fluid inlet, a suction inlet and a mixture outlet, the motive fluid inlet being connected to the air outlet of the air-separating unit and the suction inlet being connected to the liquid outlet of the solid-separating unit, wherein the mixture outlet of the jet pump is configured to be connected with a suction machine,
wherein the air-separating unit is arranged above the solid-separating unit,
wherein the liquid outlet of the solid-separating unit is connected to a suction pipe with a lower end hanging down into the collection tank, the lower end of the suction pipe being covered by a filter body, and,
wherein the air-separating unit comprises a float which is raised if liquid rises back from the solid-separating unit, when the solid-particles in the solid-separating unit have reached a maximum fill level.

21. A separator for removing solid particles from a mixture of air, liquid and solid particles, comprising:
a solid-separating unit configured to separate solid particles from a two-phase mixture of liquid and solid particles and to retain the separated solid particles in a collection tank, wherein the solid-separating unit has a mixture inlet and a liquid outlet;
an air-separating unit having an air outlet and a mixture outlet, wherein the mixture outlet is connected to the mixture inlet of the solid-separating unit; and,
a jet pump having a motive fluid inlet, a suction inlet and a mixture outlet, the motive fluid inlet being connected to the air outlet of the air-separating unit and the suction inlet being connected to the liquid outlet of the solid-separating unit, wherein the mixture outlet of the jet pump is configured to be connected with a suction machine,
wherein the air-separating unit comprises a cyclone,
wherein the air-separating unit comprises afloat which is raised if liquid rises back from the solid-separating unit, when the solid-particles in the solid-separating unit have reached a maximum fill level, and,
wherein the jet pump comprises an injector which tapers and projects with an annular gap into a collector which as well tapers, wherein the injector is connected to the motive fluid inlet, the annular gap is connected to the suction inlet and the collector is connected to the mixture outlet of the jet pump.

* * * * *